United States Patent
Bova et al.

(10) Patent No.: US 7,024,237 B1
(45) Date of Patent: Apr. 4, 2006

(54) MASK SYSTEM AND METHOD FOR STEREOTACTIC RADIOTHERAPY AND IMAGE GUIDED PROCEDURES

(75) Inventors: Frank J. Bova, Gainesville, FL (US); William A. Friedman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1325 days.

(21) Appl. No.: 09/430,034

(22) Filed: Oct. 29, 1999

(51) Int. Cl.
*A61B 5/00* (2006.01)

(52) U.S. Cl. ........................ 600/429; 606/130

(58) Field of Classification Search ............... 600/426, 600/407, 427, 429, 411, 414, 415, 417; 606/130
See application file for complete search history.

(56) References Cited

U.S. PATENT DOCUMENTS

| | | | | |
|---|---|---|---|---|
| 5,370,117 A | * | 12/1994 | McLaurin | 128/653.1 |
| 5,617,857 A | * | 4/1997 | Chader et al. | 128/653.1 |
| 5,682,890 A | * | 11/1997 | Kormos et al. | 128/653.2 |
| 6,122,541 A | * | 9/2000 | Cosman et al. | 600/426 |

\* cited by examiner

*Primary Examiner*—Eleni Mantis Mercader
(74) *Attorney, Agent, or Firm*—Dennis P. Clarke; Miles & Stockbridge P.C.

(57) ABSTRACT

Repeat fixation for medical procedures is accomplished using a non-invasive locator, specifically a face mask. The face mask has at least three fiducial markers on it. By detecting the position of the markers, the position of features within the patient can be determined with great precision. The features can be the location of head or neck cancer or other target to which radiation or other medical procedure is to be applied. Since the face mask has been molded to uniquely fit to the patient's face, it may be removed after an initial imaging of the patient. The face mask may then be re-attached one or more times to the teeth. The face mask is molded to conform to the patient's face by using thermoplastic material.

23 Claims, 2 Drawing Sheets

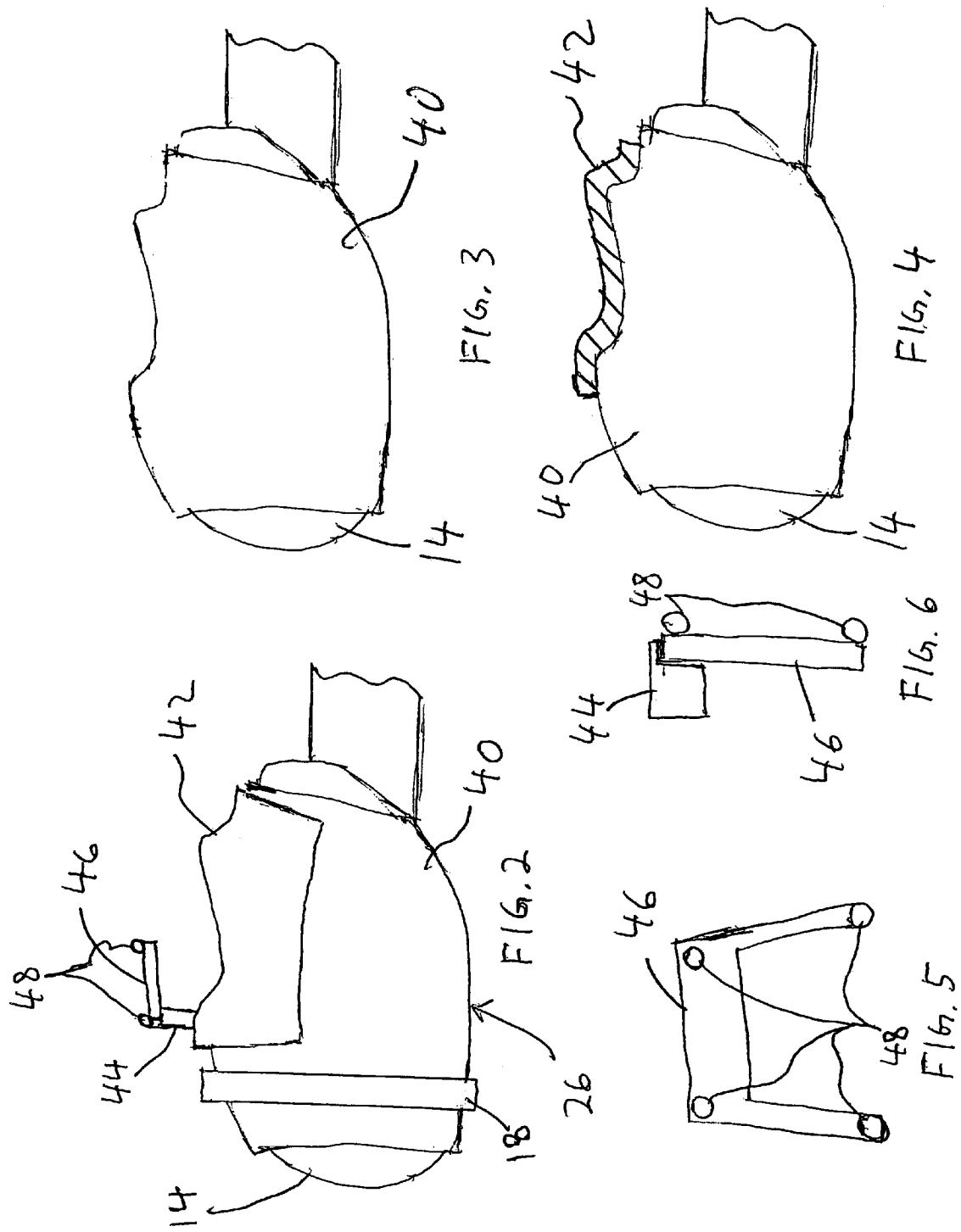

MASK SYSTEM AND METHOD FOR STEREOTACTIC RADIOTHERAPY AND IMAGE GUIDED PROCEDURES

BACKGROUND OF THE INVENTION

The present invention relates to a device, system and method for stereotactic medical procedures. More specifically, it provides for accurate positioning (fixation) of a patient or part of a patient for carrying out medical procedures, singly or multiple times.

The discussion below will initially focus on medical procedures where the procedure is performed multiple times on the same patient.

Various medical procedures involve repeated treatments at different times. For example, application of radiation is sometimes used for treating cancer or other conditions. Although a single application of radiation may sometimes be used, under many circumstances there are sound medical reasons to use repeated application of radiation at different times.

There are other medical procedures where precise location of patient features are required either for a one time therapeutic treatment or a repeated treatment.

There are situations when the localization procedure and the therapeutic procedure must be carried out at either different times or at different locations, such as a CT scan or MR scan followed by a surgical or radiosurgical procedure.

Radiosurgical technique, among other medical procedures, uses stereotactic principles for targeting, localization and treatment. The procedure begins with a stereotactic reference system being fixed to the patient's skull. This reference system remains fixed relative to all intracranial points throughout the entire radiosurgical procedure. All diagnostic exams, such as angiography, CT and MR scanning include a set of fiducial markers which allow all points within the image to be localized relative to the stereotactic reference frame. All of these fiducial system attach to the stereotactic frame in a precision and reproducible manner.

The present inventors' prior U.S. patents listed below, assigned to the assignee of the present application, and hereby incorporated by reference disclose techniques for providing stereotactic radiosurgery with a high degree of precision: U.S. Pat. No. 5,027,818 issued Jul. 2, 1991, titled DOSIMETRIC TECHNIQUE FOR STEREOTACTIC RADIOSURGERY; and U.S. Pat. No. 5,189,687 issued Feb. 23, 1993 APPARATUS FOR STEREO-TACTIC RADIOSURGERY. The techniques of the inventors' above patents allow the patient to be precisely positioned relative to radiation beams of stereotactic radiosurgery to within 0.2 mm plus or minus 0.1 mm. Although this works very well for single fraction therapy, there exist clinical settings where fractionating the total dose, i.e. dividing the dose into many small fractions, would yield additional therapeutic advantage. In the radiotherapy procedure, once the reference frame has been removed from the patient the relationship between intracranial target points and the reference system is lost. Because the above procedure would require the reference frame to remain fixed to the patient's skull through the entire course of treatment, which may last several weeks, this approach is considered inappropriate for fractionated therapy. Alternately, each fractional treatment would require a laborious and time-consuming procedure to re-determine patient position for second and subsequent treatments.

Another setting would be where the patient undergoes a medical imaging procedure to be followed by stereotactic or optic guided surgery. In this setting the patient is scanned prior, sometimes a day or two before, the surgical procedure. The registration of the patient's scan data set to their position on the operative setting is carried out through the use of surface fiducials. This usually entails the shaving of the patient head.

There exist several different techniques for non-invasive repeat fixation. These methods can be broken down into three basic categories. These are bite plate systems, contour realignment systems and mask systems. All of these systems have design flaws which can lead to unacceptable, and undetectable, positional errors.

The mask techniques have been used in radiation therapy for over three decades. In these systems a custom mask, which snugly fits either the face or the entire head, is fabricated. For high precision radiotherapy the mask is then attached to a stereotactic reference frame, similar to the frame used for any stereotactic procedure. Prior to each diagnostic exam the patient is placed into the mask/frame system and normal stereotactic fiducial systems are used for image registration.

Mask immobilization and repositioning systems have been used extensively in radiation therapy. By using the mask for both localization (i.e., determination of position and orientation) and positioning (i.e., the mask or mechanisms rigidly secured to it are used to move the patient), the positioning puts loads (forces and/or moments) on the mask which may distort it. Distorting the mask introduces errors which hinder accuracy of localization.

When performing fractionated radiotherapy, accuracy in applying the radiation is very important. Some tumors or other conditions require that the radiation be concentrated in relatively small volumes. Misalignment of the radiation beam may cause an insufficient amount of radiation to be applied to the tumor or other target. Further, such misalignment may increase the likelihood and/or degree of damage to healthy tissue adjacent the tumor or other target.

Fractionated radiotherapy may be imprecise if the tumor or other target cannot be localized with a sufficient degree of accuracy. However, this need for proper localization is the same need which one has when performing single dose radiotherapy and this need is addressed by the present inventors' two first listed below incorporated by reference patents. The additional factor in fractionated radiotherapy is the need to easily and accurately repeat a position of the patient. If the position of the patient was accurate relative to the first treatment, and relative to the imaged data set used to design the treatment, the repositioning should normally cause the patient to assume the exact same position (relative to the treatment mechanism) for the second and subsequent treatments. However, if the second or other subsequent treatment is performed with the patient only slightly moved from the first treatment position, this will introduce inaccuracies. The repeat fixation techniques discussed above have the indicated disadvantages.

More generally, the need for repeat fixation of a patient or portion of a patient exists outside of radiotherapy. In the general case, one wishes to perform a first medical procedure on a patient with a precise localization of portions of the patient, and, at some later time, perform a second medical procedure on the patient with a precise localization of portions of the patient. One can repeat laborious and time-consuming localization steps for the second medical procedure, but this increases medical costs and complexity. As used herein, a medical procedure is a procedure for diagnostic and/or remedial purposes.

In some situations, a single medical treatment without a need for repeat fixation is the desired course of treatment.

However, a high degree of accuracy in positioning may still be required. The mechanical arrangements and the associated techniques of the present inventors' last mentioned above two above incorporated by reference patents can provide a high degree of accuracy in positioning of the patient relative to the medical apparatus.

The present inventors' prior U.S. patents listed below, assigned to the assignee of the present application, and hereby incorporated by reference disclose techniques for providing determination of patient position with a high degree of precision for stereotactic radiosurgery and other medical procedures: U.S. Pat. No. 5,954,647 issued Sep. 21, 1999, titled MARKER SYSTEM AND RELATED STEREOTACTIC PROCEDURE; and U.S. Pat. No. 5,588,430 issued Feb. 14, 1995 titled REPEAT FIXATION FOR FRAMELESS STEREOTACTIC PROCEDURE. These patents disclose various locators using bite plates, head rings, and/or masks. The bite plates are used for repeat fixation medical procedures (i.e., where procedure is performed with locator on patient, locator and any other associated parts are then removed from the patient, and, at a later time, locator is placed back on patient).

It is now common for medical clinicians to obtain high contrast and high spatial resolution computerized tomography (CT) and magnetic resonance (MR) data sets. These data sets can be obtained with high spatial resolution between contiguous image slices. These data sets allow for the reconstruction of a precise 3-dimensional (3D) model that accurately describes both the patient's external and internal anatomy. The patient specific models can be manipulated to provide reconstructed views along orthogonal or oblique planes through the patient's anatomy. These computed views allow for clinicians to carry out virtual treatments (or virtual planning) to better optimize therapy for a patient.

Virtual planning is used in several different types of therapy. Radiosurgery, stereotactic radiation therapy, and routine radiotherapy are all therapies that rely upon virtual planning to position radiation beams. Image guided surgery relies upon virtual planning to allow the surgeon to design and evaluate various surgical approaches and to target specific tissues. The virtual planning process places a unique requirement on the basic 3D image data set, that being the ability to track the patient, at the time of therapy, relative to the therapeutic tool. For radiosurgery, stereotactic radiation therapy and radiation therapy, the therapeutic tool is the radiation-generating device, most commonly, a medical linear accelerator. In the case of image guided surgery, the therapeutic tool can be one of a number of devices that the surgeon my use. For example, scalpels, biopsy needles, and operating microscopes are a few of the most commonly guided surgical tools.

In order to provide the required patient-tool tracking both the tool's position and the patient's position must be known. The most common method of tracking the patient is to place identifiable reference markers, called fiducial markers, fixed relative to the portion of the patient where treatment is desired. These markers are incorporated into the 3D image data set. They are also available for identification, again on the surface of the patient (fixed relative to the portion of the patient), at the time of the therapeutic procedure. The markers on the patient are registered against their images in the 3D data set. This registration allows the computation of a rigid relationship between the virtual 3D patient and the real patient. Once this registration has been carried out, any movement of the patient can be tracked.

The last two above listed patents of the present inventors disclose, among other systems, methods and devices, a technique using a bite plate as part of a locator. Advantageously, the preferred embodiments of that bite plate are independent of the system used to immobilize (secure in a stable position) and/or move the patient. These bite plates have been quite effective and useful, especially in providing precise position and orientation for the treatment of intracranial tumors. The bite plates were molded to fit the patient's teeth (gums if the patient lacks teeth) and provide a set of fiducial markers located outside the oral cavity. An infrared tracking device views the fiducial markers (also called fiducials) and reports their location relative to the linear accelerator's x-ray beam. The fiducials allow the tracking system to continuously view the reference and thereby provide for real time feedback on the patient's position.

Although the bite plate locator technique has worked quite well for patients with intra-cranial targets, it is not as well suited for other patients. For example, patients that require therapies that significantly irritate the oral cavity can have trouble keeping the bite plate in position. Radiation therapy for head and neck cancer is one of a number of such therapies that often produce severe oral cavity inflammation.

OBJECTS AND SUMMARY OF THE INVENTION

Accordingly, it is a primary object of the present invention to provide a new and improved method and system for localization (i.e., proper relative positioning of a patient and a medical apparatus or system) in performing medical procedures.

A more specific object of the present invention is to provide precise and easy localization of a patient on which a medical procedure is to be performed.

Another specific object of the present invention is to provide precise and easy localization of a patient without requiring placement of a bite plate in a patient's mouth.

Another object is to provide for highly precise non-invasive repeat fixation for repeating medical procedures.

A further object of the present invention is to provide repeat fixation in which a locator is mechanically independent from any structures used for positioning the patient. That is, any structure used to position the patient does not move the locator except by way of the patient.

Yet another object of the present invention is to provide repeat fixation for stereotactic radiotherapy.

A further object of the present invention is to provide repeat fixation which allows relatively fast re-localization of a patient after an initial localization.

Yet another object of the present invention is to provide repeat fixation which minimizes or avoids the disadvantages of prior techniques discussed above.

A further object of the present invention is to provide an accurate localization for a one treatment medical procedure where the relative position of the patient and a medical apparatus or system may be easily adjusted to achieve a desired relative position of the patient and a medical apparatus or system.

The above and other features of the present invention which will be more readily understood when the following detailed description is considered in conjunction with the accompanying drawings are realized by a medical method including the steps, not necessarily in order, of: positioning a patient for a first medical procedure; molding a locator to external features of a patient, the locator being placed in registry with a portion of the patient; using at least 3 fiducial markers that are fixed relative to the locator a first time to get precise positioning information relative to at least part of the patient, the locator remaining mechanically free during this step; performing a first medical procedure on the patient, the locator remaining mechanically free during this step; after the first medical procedure, removing the locator from the patient; at a later time after the removing of the locator, re-attaching the locator to the patient, the locator again being in registry with the portion of the patient and having an identical orientation relative to the portion of the patient as when the locator was previously attached; after the re-attaching step, using the fiducial markers a second time to get precise positioning information relative to the at least part of the patient, the locator remaining mechanically free during this step; and after the re-attaching step, performing a second medical procedure on the patient, the locator remaining mechanically free during this step.

In more specific aspects of the invention, before performing the second medical procedure, the patient is positioned using a positioner independent of the locator to adjust and secure at least the portion of the patient in a desired position. The attaching and re-attaching of the locator is non-invasive. The locator is a face mask molded to fit in registry with the face of a specific patient. The face mask includes thermoplastic and the molding step includes the substeps of heating the thermoplastic and placing it on the face of a patient. After the molding step, the at least 3 fiducial markers are attached to the locator. The at least 3 fiducial markers are on a marker support and the attaching step includes fixing the marker support to the locator.

The present invention may alternately be described as a method for performing a diagnostic imaging or a therapeutic medical procedure includes the steps of, not necessarily in order: putting a mechanically free locator on a patient, the locator including a face mask having at least 3 fiducial markers thereon; placing the patient adjacent a medical device operable for performing the diagnostic imaging or therapeutic medical procedure on a patient, the locator remaining mechanically free during this step; and sensing the positions of the fiducial markers when the patient is in a position for performing the diagnostic imaging or therapeutic medical procedure using the medical device, the locator remaining mechanically free during this step.

In more specific aspects of the invention, the face mask is molded to fit to the face of a specific patient. The molding step is performed by the placing of the face mask on the face of a specific patient. After the molding step, the at least 3 fiducial markers are attached to the locator. The at least 3 fiducial markers are on a marker support and the attaching step includes fixing the marker support to the locator.

The present invention may alternately be described as a method of making a medical device that is a mechanically free locator including the steps of, not necessarily in order: providing a locator having a face portion; molding the face portion into a face mask corresponding to the face of a specific person and operable to register with the face of the specific person; and attaching at least 3 fiducial markers to the face mask, the fiducial markers operable to provide precise determination of the position of the patient.

The present invention may alternately be described as a system for medical procedures. The system includes: a locator attachable to a patient, having at least 3 fiducial markers thereon, and having a registration portion for registration with a portion of a patient's body. The locator being mechanically free such that a patient is positionable without applying forces to the locator during patient positioning. The locator is molded to fit external features of a specific patient.

In more specific aspects of the invention, the system includes a sensing subsystem for sensing the position of the at least 3 fiducial markers and an apparatus for applying therapeutic treatment to a patient. The sensing subsystem is operable to allow proper positioning of the patient in order to apply the therapeutic treatment to specific portions of the patient. The locator is a face mask molded to fit in registry with the face of a specific patient. The registration portion allows removal of the locator from the patient and re-attachment to the patient with an identical orientation relative to the portion of the patient as when the locator was previously attached.

The present invention may alternately be described as a system for medical procedures including: a locator attachable to a patient, having at least 3 fiducial markers thereon; a medical device for performing a diagnostic imaging or a therapeutic medical procedure on a patient; and a sensing subsystem for sensing the positions of the fiducial markers when the patient is in a position for performing the medical procedure using the medical device. The locator has a registration portion for registration with a portion of a patient's body, the locator being mechanically free such that a patient is positionable without applying forces to the locator during patient positioning. The locator is molded to fit external features of a specific patient.

In more specific aspects of the invention, the locator is a face mask molded to fit in registry with the face of a specific patient. The registration portion allows removal of the locator from the patient and re-attachment to the patient with an identical orientation relative to the portion of the patient as when the locator was previously attached. The face mask includes thermoplastic molded to fit the face of a patient. More generally, the locator includes thermoplastic molded to fit a portion a portion of a patient.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 2 is a side view of a patient's head with a head ring and the locator of the present invention;

FIG. 3 is a side view of a patient's head with an elastic piece around it, the elastic piece used in making a locator according to the present invention;

FIG. 4 is a side view of a patient's head with the elastic piece around it and showing a thermoplastic mask in cross section, the mask being placed on the patient's face in order to mold in registry therewith;

FIG. 5 is a planar view of a fiducial support and fiducial markers; and

FIG. 6 is a side view of the fiducial support and fiducial markers of FIG. 5.

DETAILED DESCRIPTION

Figure 1:
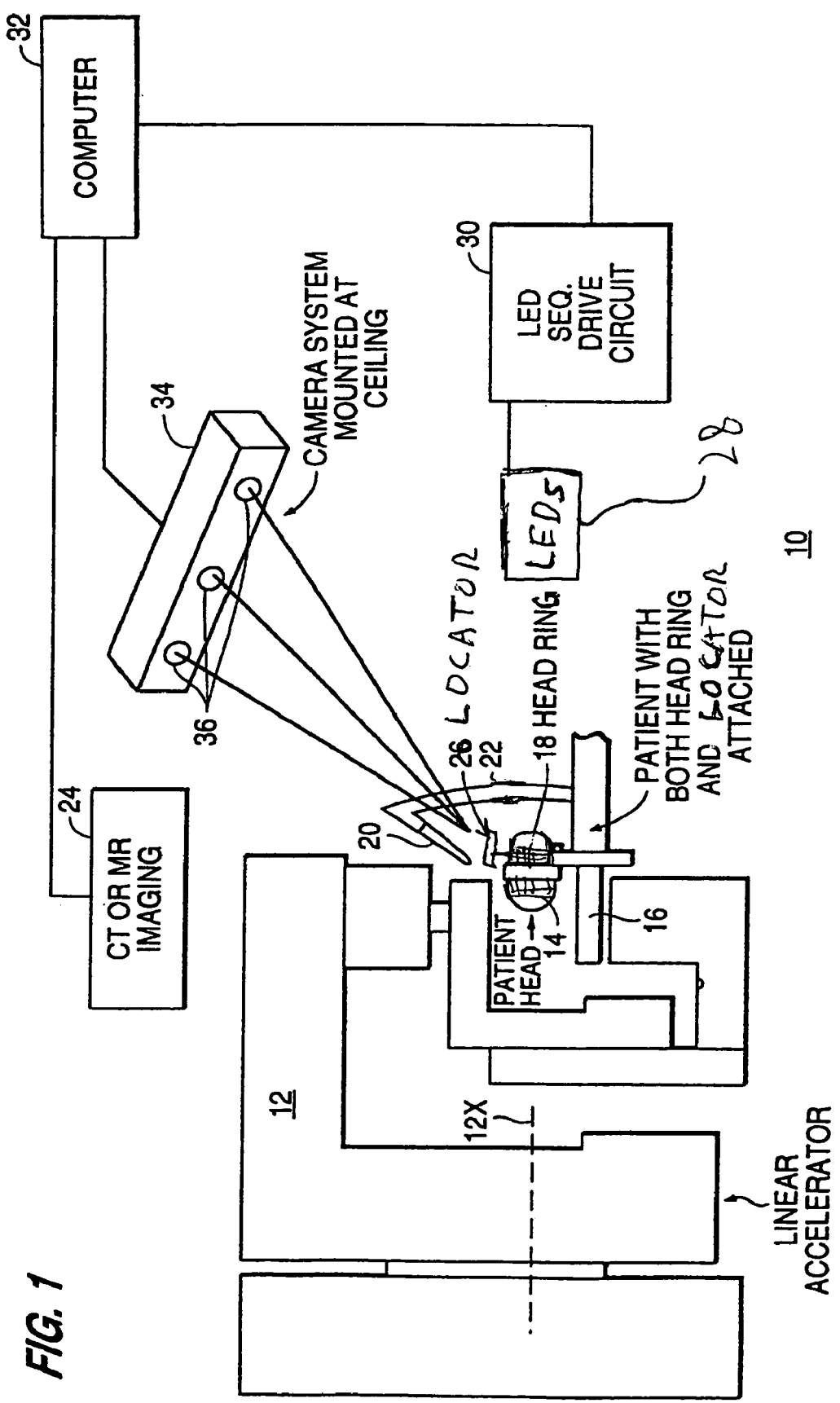
FIG. 1 is a simplified diagram of the system of the present invention.

The system 10 of the present invention is shown in FIG. 1 as having a linear accelerator 12 for performing stereotactic radiotherapy on a patient's head 14 (rest of patient's body not shown for ease of illustration) which is on a surgical table 16 (shown only partially) and secured thereto by way of a head ring 18. The details of the accelerator 12 and table 16 are not a necessary part of the present invention and need not be discussed. Moreover, these can be constructed and operable in the manner discussed with respect to the structures and techniques of the first two above incorporated by reference U.S. Patents of the inventors, this allowing the precision application of radiotherapy to the patient. As an alternative or additionally to the accelerator 12, a probe 20 (constructed in known fashion) for stereotactic surgery may be mounted to anchor 22 secured to the table 16 as shown or to a wall or other structure such as a linear accelerator, CT, MR, or any other reference required (not shown). The probe 20, which is a scalpel, laser, or other surgical apparatus, may alternately have LEDs thereon for sensing the exact position and direction (orientation) of the probe in space using known techniques such that the probe need not be attached to anything) A further alternative or additional feature may be an imaging system such as computerized tomography (CT) or magnetic resonance (MR) system 24. One or more of the accelerator 12, probe 20, and imaging system 24 are used to perform medical procedures on the patient.

The present invention provides for repeated fixation of a locator in registry with (i.e., uniquely positioned relative to) a portion of a patient. Before discussing details of how this is accomplished, it will generally be noted that the locator is used to provide a frame of reference for performing a first medical procedure and the locator is then removed. The locator is then re-attached to the patient such that a second medical procedure could be performed. The medical procedures may be any diagnostic and/or treatment procedures. However, the discussion which follows will emphasize use of the technique for fractionated stereotactic radiotherapy for head cancer or neck cancer. However, other therapeutic techniques (as opposed to purely diagnostic techniques) could also be used.

The present system uses a locator 26 having a face mask with passive fiducial markers as will be discussed in more detail below. One or more light emitting diodes or LEDs 28 may be connected to an LED sequential drive circuit 30. The LED or LEDs 28 can be used to generate light pulses that reflect off the fiducial markers in order to detect the precise position of the locator 26 and in turn precisely determine the position of at least a portion of the patient that is to be treated. (Alternately, the LEDs 28 could be the fiducial markers on the locator 26 in the fashion of FIG. 1 of the present inventors' above noted '647 patent.) Circuit 30 is also connected to a computer 32. The computer is connected to the imaging system 24 and a camera system 34. The camera system 34, which serves as a sensing subsystem, may be of a known type having several cameras 36 as part thereof in order to locate the bite plate 26 by way of several LEDs (not shown in FIG. 1) thereon. The camera system 34 and technique for strobing the LEDs (sequentially lighting them one at a time) may be that disclosed in U.S. Pat. No. 5,198,877, issued to Schulz on Mar. 30, 1993, assigned on its face to PixSys, Inc, and hereby incorporated by reference. Such a camera system is commercially available from PixSys, Inc.

Except as otherwise noted, the components of FIG. 1 are constructed and operable in the same fashion as the corresponding components of FIG. 1 of the incorporated by reference '647 patent. Significantly, the present invention uses a different locator 26 construction from that used in the '647 patent.

With reference now to FIG. 2, the patient's head 14 is restrained and can be positioned by use of a head ring 18, which ring would then be fixed in place using techniques discussed in the present inventors' incorporated by reference patents. The head ring 18 may be of any type used or developed to constrain the head. The head ring 18 may be considered a positioner for positioning the patient's head.

As shown in FIG. 2, the locator 26 includes an elastic base 40 made of gauze or similar flexible or textile material, a face mask 42 molded to fit in registry with the face (thus serving as a registration portion) of a specific patient, an offset mount 44 attached to the face mask 42 and made of LUCITE or other material, a reference array support (preferably made of rigid carbon fiber) 46 attached to offset mount 44, and at least 3 (preferably 4) fiducial markers 48 fixed to the support 46. The fiducial markers may be spherical reflectors such that light from LEDs 28 (FIG. 1 only) are reflected. The reflections allow precise determination of the position and orientation of the support 26 and in turn determination of the precise position and orientation of a portion of the patient (specifically and preferably including the head).

Turning now to FIGS. 3–6, the process of constructing the locator 26 of the present invention will be discussed. The elastic base 40 is flexible, fabric material such as gauze. It may be tubular or otherwise arranged in a tube and placed around a patient with the front tending to generally conform to the patient's face. This may extend to cover the face or it may be designed so that it extends to the edge of the face providing attachment to the face mask to provide the small amount of force necessary to keep the mask in contact with the patient's surface. A piece of thermoplastic material is heated, for example by placement in hot water (not shown) to make it pliable. After draining the water off of the thermoplastic material, it is placed on top of the face of the patient with the front of the base 40 between it and the patient's face. The thermoplastic material hardens into the face mask 42 (FIG. 4, and as previously shown in FIG. 2). Alternately, the thermoplastic mask may be replaced with a plaster mask or any other material which allow for a rigid mold of the patients surface to be taken.

Following FIG. 4, the support 46 with fiducial markers 48 is mounted to the mask 42 by way of offset mount 44. The offset mount 44 is secured to support 46 by one or more screws (not shown) or any other arrangement to maintain stable connection between mount 44 and support 46. The mount 44 would then be adhered to the mask 42 by silicone or other adhesive. The result is the completed locator 26. Note that the support 46 could be mounted to the thermoplastic before it is molded into face mask 42, or attached to the face mask 42 when it is on the patient or when it has been removed from the patient. It should also be noted that the mask can be made and then attached to a system that allow the small pressure required to keep the mask in contact with the patient's surface.

With reference to FIG. 2, the flexibility of base 40 is such that securing or positioning the patient's head by use of head ring 18 will not significantly load (i.e., transfer force or moments to) the face mask 42. However, one could alternately use a smaller base 40 such that it does not extend between the head ring 18 and the skin of the patient. Moreover, the head ring is optional and not a necessary part of the present invention. Other arrangements for stabilizing the position of the patient's head could be used. Further, some medical procedures may not require any mechanism to stabilize the patient's head. If a medical procedure is sufficiently fast, simply telling the patient to stay still may give the doctors the necessary stability. Importantly, the mask is only used to determine the position and orientation of the patient, but is not used to apply force to reposition or move the patient and the mask is mechanical free of any mechanism used to apply force for moving or positioning the patient. The mask and fiducial system thereby allows dynamic referencing of the patient relative to the imaging or other medical apparatus. This allows the mask to avoid or minimize the chance of distortion errors and avoid or minimize errors when the mask is reseated (placed back in registry with) on the patient's face for a treatment session after the first treatment session. The first treatment session could be therapeutic or simply data gathering (diagnostic or mapping, i.e., collecting 3D data set).

If one is using the locator 26 of FIG. 2 for repeated medical treatment such as fractional radiotherapy for head or neck cancer, the locator can be completely removed from the patient. When the patient comes back for the next treatment, the locator 26 can be placed back in an identical position (i.e., relative to the patient's face) by putting the face mask 42 back into registry with the face. Image data from one treatment session can be registered to image date from another treatment session by virtue of re-application of the mask in the same location at each treatment session.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A system for medical procedures, the system comprising:
    a locator attachable to a patient, having at least 3 fiducial markers thereon;
    a medical device for performing a diagnostic imaging or a therapeutic medical procedure on a patient; and
    a sensing subsystem for sensing the positions of the fiducial markers when the patient is in a position for performing the medical procedure using the medical device; and
    wherein the locator has a registration portion for registration with a portion of a patient's body, the locator being mechanically free such that a patient is positionable without applying forces to the locator during patient positioning; and wherein the locator is molded to fit external features of a specific patient.

2. The system of claim 1 wherein the locator is a face mask molded to fit in registry with the face of a specific patient.

3. The system of claim 2 wherein the registration portion allows removal of the locator from the patient and re-attachment to the patient with an identical orientation relative to the portion of the patient as when the locator was previously attached.

4. The system of claim 3 wherein the face mask includes thermoplastic molded to fit the face of a patient.

5. The system of claim 1 wherein the locator includes thermoplastic molded to fit a portion a portion of a patient.

6. A medical method comprising the steps, not necessarily in order, of positioning a patient for a first medical procedure;
    molding a locator to external features of a patient, the locator being placed in registry with a portion of the patient;
    using at least 3 fiducial markers that are fixed relative to the locator a first time to get precise positioning information relative to at least part of the patient, the locator remaining mechanically free during this step;
    performing a first medical procedure on the patient, the locator remaining mechanically free during this step;
    after the first medical procedure, removing the locator from the patient;
    at a later time after the removing of the locator, reattaching the locator to the patient, the locator again being in registry with the portion of the patient and having an identical relative to the portion of the patient as when the locator was previously attached;
    after the re-attaching step, using the fiducial markers a second time to get precise positioning information relative to the at least part of the patient, the locator remaining mechanically free during this step; and
    after the re-attaching step, performing a second medical procedure on the patient, the locator remaining mechanically free during this step.

7. The medical method of claim 6 wherein;
    before performing the second medical procedure, the patient is positioned using a positioner independent of the locator to adjust and secure at least the portion of the patient in a desired position.

8. The medical method of claim 6 wherein the attaching and re-attaching of the locator is non-invasive.

9. The medical method of claim 8 wherein the locator is a face mask molded to fit in registry with the face of a specific patient.

10. The medical method of claim 9 wherein the face mask includes thermoplastic and the molding step includes the substeps of heating the thermoplastic and placing it on the face of a patient.

11. The medical method of claim 10 further comprising the step of, after the molding step, attaching the at least 3 fiducial markers to the locator.

12. The medical method of claim 11 wherein the at least 3 fiducial markers are on a marker support and the attaching step includes fixing the marker support to the locator.

13. The medical method of claim 6 wherein the locator is a face mask molded to fit in registry with the face of a specific patient, and further comprising the step of, after the molding step, attaching the at least 3 fiducial markers to the locator.

14. A method for performing a diagnostic imaging or a therapeutic medical procedure comprising the steps of, not necessarily in order:
    putting a mechanically free locator on a patient, the locator including a face mask having at least 3 fiducial markers thereon;
    placing the patient adjacent a medical device operable for performing the diagnostic imaging or therapeutic medical procedure on a patient, the locator remaining mechanically free during this step; and
    sensing the positions of the fiducial markers when the patient is in a position for performing the diagnostic imaging or therapeutic medical procedure using the medical device, the locator remaining mechanically free during this step.

15. The method of claim 14 further comprising the step of molding the face mask to fit to the face of a specific patient.

16. The method of claim 15 wherein the molding step is performed by the placing of the face mask on the face of a specific patient.

17. The method of claim 16 further comprising the step of, after the molding step, attaching the at least 3 fiducial markers to the locator.

18. The medical method of claim 17 wherein the at least 3 fiducial markers are on a marker support and the attaching step includes fixing the marker support to the locator.

19. A method of making a medical device that is a mechanically free locator comprising the steps of, not necessarily in order:
providing a locator having a face portion;
molding the face portion into a face mask corresponding to the face of a specific person and operable to register with the face of the specific person; and attaching at least 3 fiducial markers to the face mask, the fiducial markers operable to provide precise determination of the position of the patient.

20. A system for medical procedures, the system comprising:
a locator attachable to a patient, having at least 3 fiducial markers thereon, and having a registration portion for registration with a portion of a patient's body, the locator being mechanically free such that a patient is positionable without applying forces to the locator during patient positioning; and
wherein the locator is molded to fit external features of a specific patient.

21. The system of claim 20 further comprising a sensing subsystem for sensing the position of the at least 3 fiducial markers and an apparatus for applying therapeutic treatment to a patient; and wherein the sensing subsystem is operable to allow proper positioning of the patient in order to apply the therapeutic treatment to specific portions of the patient.

22. The system of claim 21 wherein the locator is a face mask molded to fit in registry with the face of a specific patient.

23. The system of claim 22 wherein the registration portion allows removal of the locator from the patient and re-attachment to the patient with an identical orientation relative to the portion of the patient as then the locator was previously attached.

* * * * *